United States Patent [19]

James et al.

[11] 4,303,337

[45] Dec. 1, 1981

[54] APPARATUS FOR DETERMINING HEMOGLOBIN AND WHITE BLOOD CELL COUNT IN BLOOD

[75] Inventors: Bobby D. James, Hialeah; Ronald O. Simpson; J. David Starling, both of Miami, all of Fla.

[73] Assignee: Coulter Electronics, Inc., Hialeah, Fla.

[21] Appl. No.: 23,958

[22] Filed: Mar. 26, 1979

[51] Int. Cl.³ ..................... G01N 21/01; G01N/27/04
[52] U.S. Cl. .................................. 356/72; 324/71 CP; 356/40
[58] Field of Search ......................... 356/40, 356/41, 42, 72; 324/71 CP; 250/222 PC; 364/555 364/555

[56] References Cited

U.S. PATENT DOCUMENTS

| | | | |
|---|---|---|---|
| 3,675,768 | 7/1972 | Legorreta-Sanchez | 324/71 CP |
| 3,743,424 | 7/1973 | Coulter | 356/40 |
| 4,157,499 | 6/1979 | Kacerek | 324/71 CP |
| 4,259,291 | 3/1981 | Smythe | 250/576 |

FOREIGN PATENT DOCUMENTS 2645065  4/1978  Fed. Rep. of Germany ... 119/14.41

*Primary Examiner*—John K. Corbin
*Assistant Examiner*—Bruce Y. Arnold
*Attorney, Agent, or Firm*—Silverman, Cass & Singer, Ltd.

[57] ABSTRACT

A single instrument for photometrically determining hemoglobin content and electronically determining white blood cell count of a single sample suspension of blood. The instrument is provided with a calibration mode of operation independent of the run or normal operational mode of the instrument.

A vacuum system is described where vacuum is generated during the operating cycle only at periods when vacuum is required with an adjustable volume vacuum chamber interposed in the vacuum system to assure proper vacuum levels.

Carryover of one liquid to a next introduced second liquid in the test vessel is reduced by successive draining of said second liquid and reintroduction into said vessel of a replacement amount of said second liquid. The second liquid can be a sample of rinse liquid.

An hydraulic system is described as operating in conjunction with the pneumatic or vacuum system. The hydraulic system employs additional plural solenoid operated devices, each to perform a specific operational function during the operational cycle of the instrument.

38 Claims, 10 Drawing Figures

APPARATUS FOR DETERMINING HEMOGLOBIN AND WHITE BLOOD CELL COUNT IN BLOOD

CROSS-REFERENCE TO PERTINENT PATENTS AND PATENT APPLICATIONS AND INCORPORATION THEREOF BY REFERENCE HEREIN

Reference is made to U.S. Pat. Nos. 3,927,317 of Dec. 16, 1975; 3,743,424 of July 3, 1973; 3,566,133 of Feb. 23, 1971; 3,622,795 of Nov. 23, 1971; 3,733,548 of May 15, 1973 and United States Patent Application Ser. No. 768,864 filed Feb. 15, 1977 entitled APERTURE MODULE for use in Particle Testing Apparatus, now U.S. Pat. No. 4,090,128 of May 16, 1978, each of the aforesaid being incorporated by reference and made a part hereof. All these identified patents and patent applications are owned by the Assignee hereof.

BACKGROUND OF THE INVENTION

This invention relates generally to the provision of a single instrument wherein an electronic particle study device of the Coulter type operating upon the Coulter principle is combined with apparatus for photometric measurement of hemoglobin content of a single sample of blood.

As such, the instrument is an improvement upon the instrument described in U.S. Pat. No. 3,743,424 and as well, provides hemoglobin measuring capabilities which comprise an improvement over U.S. Pat. Nos. 3,927,317 and 3,622,795.

The measurement of the hemoglobin content of blood involves the preparation of a suspension of blood cells in a saline electrolyte solution. The sample is lysed, that is, an agent is added which breaks down the red blood cells to release their content into the solution. This solution and the resulting suspension contain the coloring matter of the red blood cells and the unaffected white blood cells.

The operation of the counting device portion of the invention is disclosed in U.S. Pat. Nos. 2,656,508 and 2,869,078. The first of these describes the general principle which has been referred to above as the Coulter principle, that is, causing particles to pass through a minute aperture whose effective impedance is changed with the passage of each particle in an amount which is proportional to the size of the particle.

The apparatus which utilizes the Coulter principle directs an electric current across a scanning aperture, and detects and counts the signals produced by the particles of a known volume as they pass through the aperture. The second of these patents describes apparatus which automatically starts the operation of the counting device merely by turning a stopcock, meters the required volume to pass through the aperture, and then turns the counting device off.

The apparatus disclosed in U.S. Pat. No. 3,743,424 included an electronic particle counting device operating on the Coulter principle which was combined with an optical hemoglobinometer such that at some step in the sequence of events of the operation of the counting device, the operation of the optical hemoglobinometer is started. The same sample suspension that is utilized in the counting device is utilized also in the hemoglobinometer by means of a thief or fluid connection from a vessel of the counting device to the hemoglobinometer. The action of the counting device in starting the hemoglobinometer is automatic.

The hemoglobinometer of said U.S. Pat. No. 3,743,424 involved the use of a standard solution which was viewed by an optical colorimeter to obtain a value of the absorbance of the standard solution. This information was stored in a suitable storage circuit and the test sample or unknown was viewed by the same colorimeter and its absorbance value compared with that of the standard solution. Thus a supply of standard solution was necessary and a quantity required to be introduced to the area traversed by the light beam of the colorimeter every time a determination was to be made upon a test sample. A manometer/syphon apparatus was utilized to move the sample suspension both through the aperture of the counting apparatus and through the hemoglobinometer. Limitations as to the quantity of standard solution available pose a significant problem to widespread use of the aforementioned combination notwithstanding its capability to provide both white cell count (WBC) and hemoglobin content (HGB).

U.S. Pat. No. 3,566,133 teaches a voltage storage and rundown circuitry for use in photometric analysis and U.S. Pat. No. 3,622,795 teaches a flow-through system for measuring the absorbance of a sequence of test samples as related to a reference liquid which is introduced sequentially alternately with the test samples, as in the combined counter and hemoglobinometer of U.S. Pat. No. 3,743,424.

According to U.S. Pat. No. 3,566,133, just prior to the introduction and measurement of each sample, a quantity of the reference liquid is fed to the photometric apparatus and its transmittance measured to provide a voltage representative thereof. Like the combined counter/hemoglobinometer, no provision was made for storing a "reference" value internally so that the use of the standard solution could be eliminated. The U.S. Pat. No. 3,927,317 provides apparatus and electrical circuitry therein which can provide an electrically stored standard value which is that of the voltage value of a blanking solution. However, the blanking solution is not a fixed standard and can vary from batch to batch as to transmittance so as to be practically an unknown itself.

Accordingly, an initial calibration adjustment must be made for each blanking solution. To accomplish such calibration, a calibration control solution is compounded having a known photometric response. Calibration is not an easy or precise operation and is subject to many variations which reduce accuracy. Error is introduced by the circuitry itself due to component aging, power fluctuations, and other common electronic variables experienced with various components and circuit conditions. It is desirable to eliminate such error and increase accuracy and precision in providing hemoglobin content measurements in any proposed combined cell counter and hemoglobinometer.

Any testing of a sequence of liquid samples presents liquid dispensing, handling, measuring and disposal problems. Where the instrument is desired to be of "flow-through" type, the various components including vessels, cuvettes, tubing, etc., require filling, rinsing, draining, refilling, etc., all in timed relationships with respect to volumetric and photometric measurements.

U.S. Pat. No. 3,622,795 teaches a flow-through photometer having a fluid handling system in which an automatically supplied rinse liquid having a known transmittance was employed as the blanking solution.

Means were provided to accomplish the measurement of hemoglobin in a lysed blood sample by manual pouring of a sequence of samples into a cuvette or test vessel alternately with automatic dispensing of the blanking solution. These described expedients still were not fully satisfactory.

In U.S. Pat. No. 3,566,133 the transmittance of the reference standard was electrically stored momentarily as a voltage applied to a storage capacitor and then discharged down to a voltage value having a predetermined value representative of a sample against which the reference is being compared. In such apparatus, the time duration of the voltage rundown was calibrated to provide a readout of the absorbance of the sample, for example. However, while this circuit was a distinct improvement over the prior art, plural introductions of the calibration solution were required to accomplish calibration of the instrument. In many apparatus where a reference value was stored, the value generally was lost when the readout was made and hence repeated full runs had to be made with a calibration solution in order to complete the calibration process. This was time consuming as well as expensive.

U.S. Pat. No. 3,927,317 provided electric circuitry for a photometer which was capable of storing the voltage value of a blanking solution for long periods of time. The blanking solution is employed initially with a calibration control solution for calibration purposes and then is employed for comparative voltage rundown measurements of a sequence of samples. Thus for calibration, the transmittance of the blanking solution is stored as a voltage on a capacitor which is permitted to discharge until equal to the voltage representative of the transmittance of a calibration solution of known or assayed HGB.

It would be highly desirable to combine with the improved hemoglobin measuring apparatus of the type disclosed in U.S. Pat. No. 3,927,317 a particle counting device of the Coulter type such as employs the counting system disclosed in U.S. Pat. No. 3,733,548. A considerable deterrent to such combination is the required use of vacuum to draw liquid suspension through the scanning aperture during the counting of particles. With the combination considered, vacuum is required generally only when necessary to move fluid through the scanning aperture. This is only a part of the proposed operating cycle. However, the vacuum systems available all require continuously generated vacuum pumps, attendant vacuum bottles, and supporting hardware. Danger of spillage and breakage accordingly are presented with such systems last described. Space utilization problems also occur which must be solved before an acceptable combined instrument can be provided which is a marketable product.

Other problems involved in the combined instrument result in operator or support personnel errors occasioned during the operation or in preparation of the necessary sample solutions. The various functional devices should be monitored with appropriate warnings provided for alerting the operator to mishaps which may occur when they occur.

Another problem which is encountered in the handling of successive samples particularly in a flow-through device is the danger of carryover of one sample to the next and/or, if the sample is emptied and replaced by rinse liquid, for example, dilution of the next sample by residual rinse liquid being left behind when the rinse liquid is drained from the test vessel, or by bubbles, etc., remaining within the drained test vessel. Carryover reduces precision and increased precision is a goal for any new instrument. While rinsing a test vessel subsequent to release of a sample therefrom is helpful in reducing carryover of one sample to the next to appear sample, there remains the problem of compensating for the possible dilution of the sample by the residual rinse liquid. It would be highly desirable materially to reduce carryover effect to the point that it will play no, or at least a negligible, part in preventing achievement of highly improved precision during operation of the combined instrument.

SUMMARY OF THE INVENTION

The invention is directed to providing means whereby an efficient, compact and precisely operating instrument for determining both WBC and HGB of a single sample suspension can be provided. In respect of the above goal, the invention provides a vacuum system wherein a vacuum generator is operated to generate a vacuum in the system only during the portions of the operating cycle where vacuum is required, for example, when particles are moved through the scanning aperture of the electronic particle counting device and other momentary functions. When not required, the vacuum in the system is released.

The invention also provides a unique method and apparatus for washing the test vessel either with the sample itself, or with rinse liquid to reduce carryover effects by effecting at least a fractional drain subsequent to introduction of a liquid into the vessel. Upon detection or at a predetermined time after introduction, drain means operates to remove at least a fraction of the sample from the test vessel. Such removal may occur during the introduction of the sample to the test vessel so that the sample can be used as a wash medium. A partial or full refill of the test vessel may be effected.

Means also are provided to define and monitor the vacuum system so as to establish operable vacuum limits during the count cycle of the instrument and also to operate an alarm to alert the operator to malfunctions.

Additional plural solenoid operated dispenser devices are provided which are operable at selected intervals during the operation cycle to perform the fill, drain and overflow, if any, removal functions utilizing the hydraulic circuitry carried within the instrument.

Means are provided to provide a repeatable readout display during calibration so reference can be made thereto while the adjustment of the potentiometer is effected varying the duration of discharge of the capacitor originally carrying the higher voltage to perform the calibration.

BRIEF DESCRIPTION OF THE DRAWINGS

FIG. 8 is a schematic representation of the pneumatic and hydraulic circuitry of the instrument embodying the invention.

DESCRIPTION OF THE PREFERRED EMBODIMENT

Figure 1:
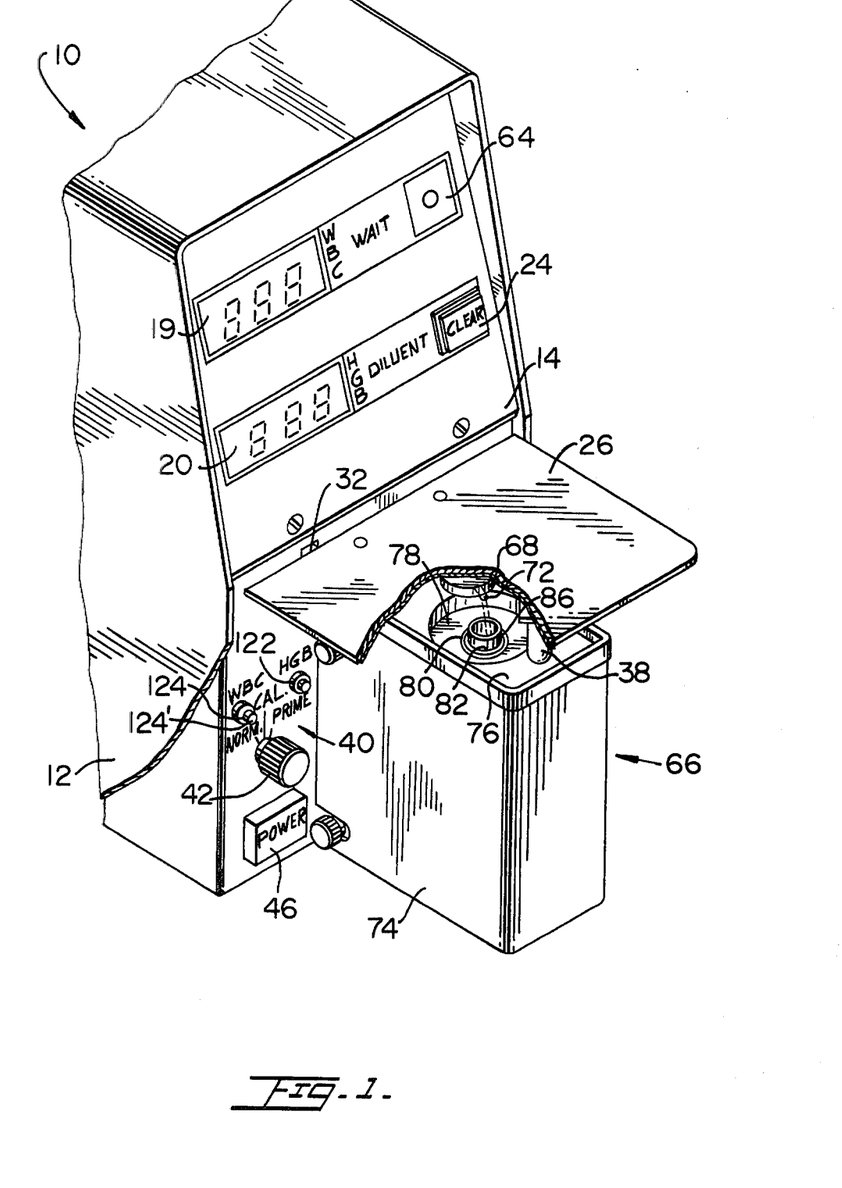
FIG. 1 is a fragmentary perspective view illustrating the apparatus embodying the invention.
Figure 2:
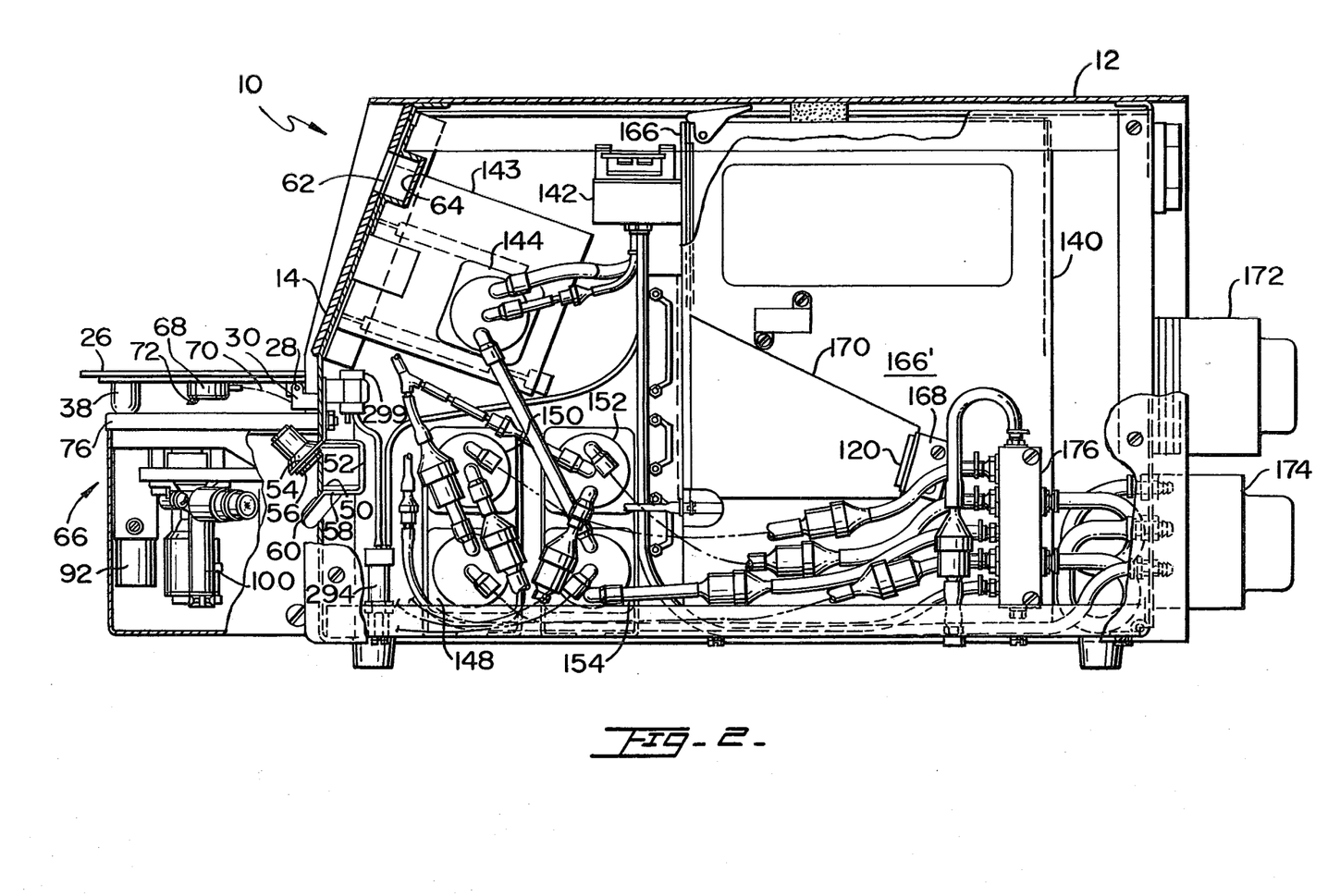
FIG. 2 is a side view of the apparatus of FIG. 1 with the housing uncovered to show interior detail.
Figure 3:
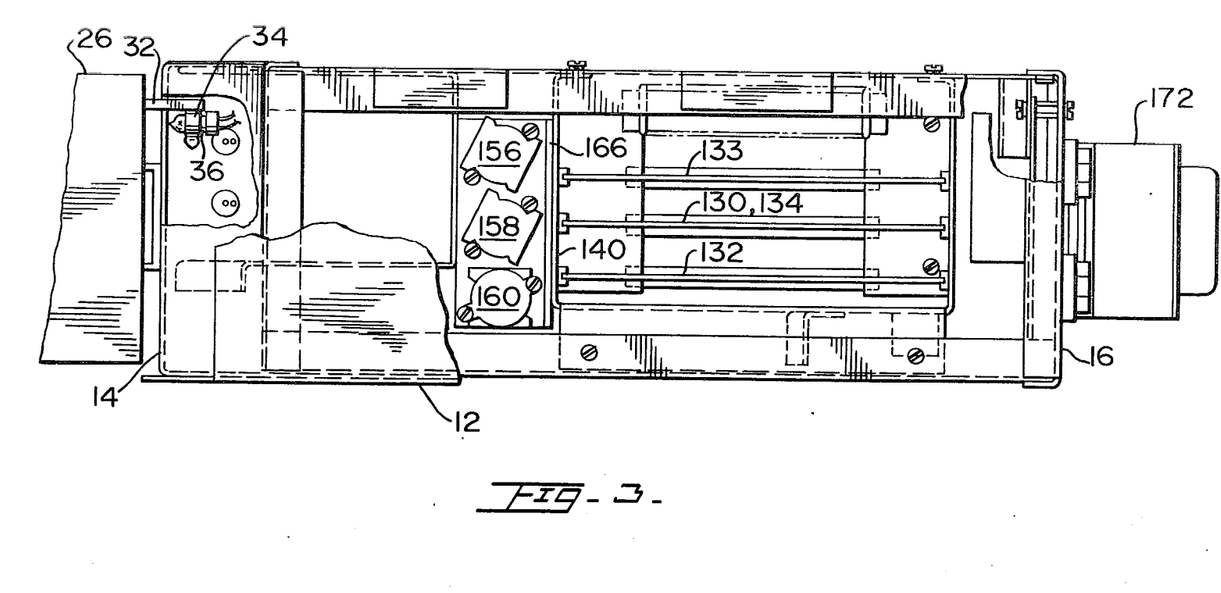
FIG. 3 is a top plan view of the apparatus of FIG. 1, portions being uncovered to show interior detail.

Referring to the drawings, the apparatus of the invention is illustrated as embodied in instrument 10 having a cabinet 12 and including front panel 14 and rear panel 16. The front panel 14 includes display windows 19 and 20 for viewing digital readout displays for WBC (White Blood Cell Count) and HGB (Hemoglobin) respectively. A push button operated switch 24 labeled "clear" is accessible through the panel 14. A lid 26 extends horizontally forward of the front panel 14. Lid 26 is mounted on a spring loaded shaft 28 arranged on lugs 30 and is pivotally movable from its normal, horizontally oriented condition to a lifted, generally vertical condition for enabling introduction of a sample to the test cuvette of the instrument 10. The lid 26 is used to initiate both fluid moving operations and quantitative measuring functions.

Bracket 32 is secured to the lid 26 and extends rearward through a suitable opening in the front panel 14 to terminate in portion 34 on which mercury switch 36 is mounted. A depending stop bumper 38 is fastened to the underside of lid 26.

A three position rotary switch 40 is operated by manipulating knob 42 from the front of the panel 14. The three positions involve the operational functions or modes (1) normal or run mode; (2) calibrate mode; and (3) prime mode: each to be described later.

A pushbutton actuator 46 for the power switch is accommodated through a suitable window formed in the front panel 14. Passage 50 is formed in front panel 14 to accommodate U-bracket 52, the upper arm 54 thereof carrying screen position adjusting mirror 56 and the lower arm 58 carrying mirror 60 for the aperture field inspection viewer, also to be described in more detail later. The front panel 14 has a window 62 to accommodate a display screen 64 for viewing the aperture area.

A test module 66 is provided as a self-contained unit housing the test vessel for holding the sample during both photometric analysis and particle count operations. The module 66 is secured to the front panel 14 of instrument 10 immediately below the lid 26. Lid 26 carries a depending dispensing head 68 coupled by flexible tube 70 to the interior fluid moving system which is arranged mounted within the cabinet 12. The bumper 38 engages the top of the module unit 66 so that the lid 26 is horizontally arranged with the dispensing head 68 having its nozzle 72 communicating to the test vessel.

An outer shroud 74 formed as a sheet metal enclosure is provided for shielding the test module 66 with suitable slots and screws provided to enable removal of said shroud to enable access to be gained to the interior operating elements thereof when desired.

The test module 66 includes a platform 76, in which a recessed well 78 is defined with the raised center ring 80 surrounding the opening of through passage 82. A drain fitting 84 opens to the well 78. Well 78 and the passage 82 may be concentric. Test vessel 86 is seated in passage 82 and is secured in place by securing bracket 88 to depending posts 89.

The optical system used for hemoglobin determination is mounted to the rigid platform 76 and includes a photodetector tube 90 sealed in a cylindrical housing 92; a lens system 94; a filter 95; a light source 96 aligned with the lens system 94 and the photodetector tube 90. The arrangement described enables a beam 98 of light to be projected through the test vessel 86 and its liquid content and the transmittance of the beam through the test vessel to be monitored by photodetector 90.

Cylindrical vessel 100 is positioned adjacent cuvette 86 and is secured side by side thereto. A through passage 102 is formed in the wall between test vessel 86 to communicate to vessel 100. A wafer 104 of insulating material such as ruby or the like, sealingly is secured to vessel 100. Wafer 104 has a controlled-dimension scanning aperture 106 formed centrally therethrough and the vessels 86 and 100 are arranged to enable aperture 106 to provide the only communication between said vessels.

A first electrode 108 is disposed within vessel 86 and in the vicinity of the aperture 106. A second electrode 112 is disposed within vessel 100 thereof and located opposite the aperture 106.

A lens 116 for focusing is arranged adjacent vessel 100 at a location aligned with the aperture 106. Mirror 60 is positioned to receive the image formed when a light beam from source 118 is projected diametrically through the test vessel 86 and vessel 100 and aligned with the aperture 106. An image representative of the vicinity of the aperture 106 is reflected by way of mirrors 60 and 56 to mirror 120 located within the cabinet 12 and thence to the viewing screen 64. The mirror 56 is mounted so that its angular orientation can be varied for positioning the aperture image on screen 64.

Adjustable potentiometers 122 and 124 are secured to the front panel 14 and are capable of being adjusted from the exterior of the cabinet 12.

Figure 5A:
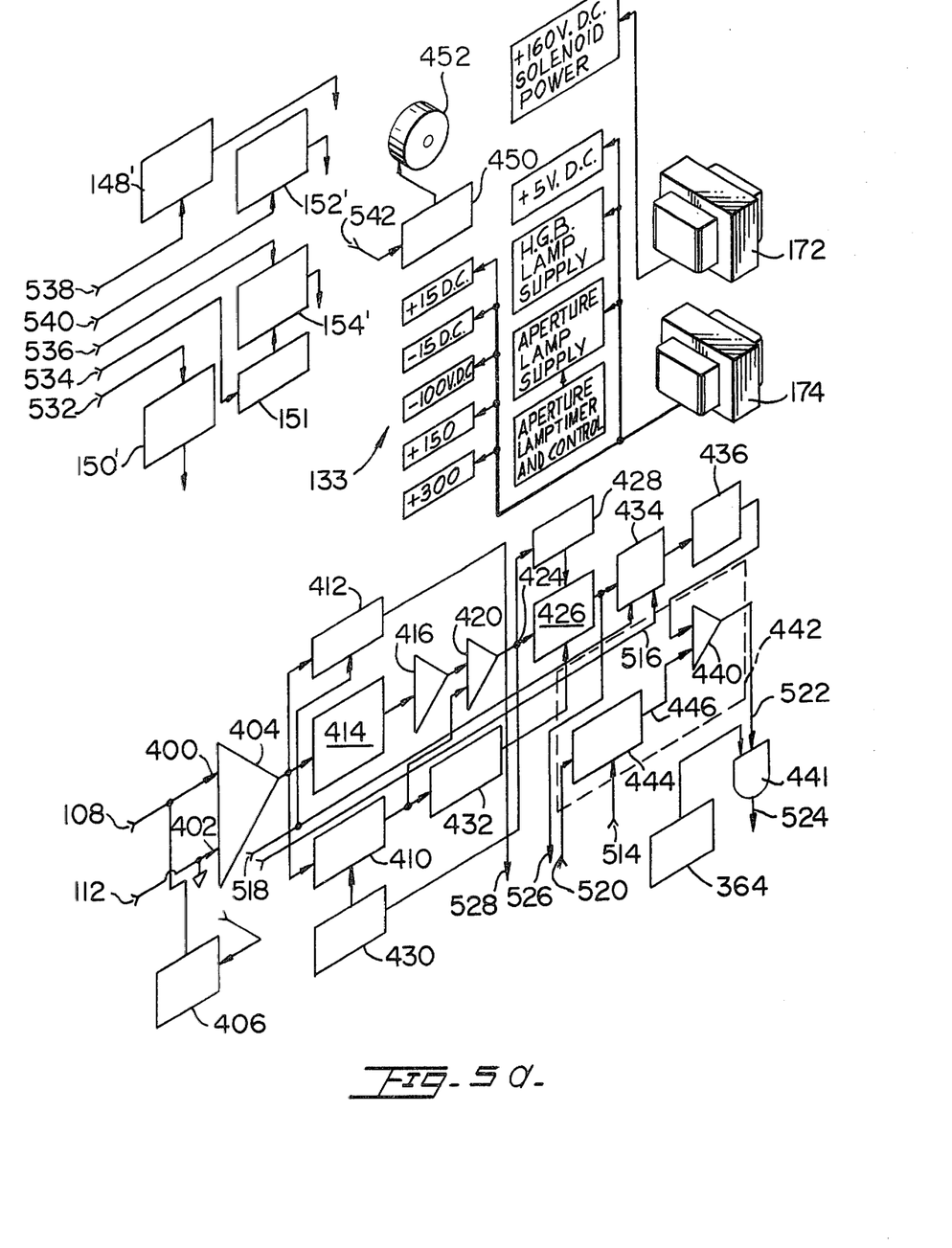
FIG. 5a is a block diagram illustrating a portion of the operational system of the instrument embodying the invention.

The cabinet 12 houses the entire electrical circuitry, including the programmer or control circuit 130 and the HGB (Hemoglobin) computing circuit 134, the WBC (White Blood Cell Count) processor circuit 132; and the power distribution circuitry 133 (illustrated in FIG. 5a). Display modules 136 and 138 for WBC and HGB readouts are provided mounted so as to be visible through windows 19 and 20 respectively of the front panel 14.

Individual fluid dispensers, their associated solenoids and solenoid controls therefor as well as the miscellaneous check valves, pneumatic and hydraulic fluid circuitry, pneumatic and hydraulic manifolds, etc., are positioned and supported within the interior of cabinet 12. The power for the solenoids and solenoid controls is obtained from power transformer 172 while the remaining power requirements are supplied by power transformer 174.

A framework stand or support 140 is erected within the cabinet 12 and mounts the printed circuit boards respectively carrying the programmer or control circuitry 130 and the HGB computing circuitry 134, the WBC processor circuitry 132, and the power distribution circuitry 133. A pneumatic manifold 142 is secured to the stand 140. A support stand 143 for the WBC readout display modules 136 and the HGB readout display module 138 respectively is provided secured within the cabinet 12 and supports, as well, an adjustable volume vacuum chamber 144 which is coupled between the manifold 142 and the vacuum generating means to be described.

Fluids are moved in the pneumatic and hydraulic systems by operation, selectively, of four solenoid operated dispensers 148, 150, 152 and 154 which are mounted within the cabinet 12.

Suitable switches 156, 158 and 160 are mounted upon the manifold 142 for monitoring two levels of vacuum in the vacuum system, and the level of rinse liquid in an exterior storage vessel 162, respectively. A waste receptacle 164 also is disposed exterior of the cabinet 12. Suitable connector mounts, etc., are secured to the vertical wall 166 of stand 140. Wall 166' of the stand 140 carries a mounting 168 for the mirror 120 including a darkened area 170 for reducing reflections which could interfere with the transmission of the aperture image by mirror 120 to the screen 64 so as to assure that the reflected image accurately represents the aperture area.

The rear panel 16 of the cabinet 12 mounts the power transformers 172 and 174 and is provided with suitable passageways and fittings to accommodate the fluid lines leading to the diluent storage vessel 162 and the waste receptacle 164. The fluid transfer manifold 176 is positioned within the cabinet 12 and is located in the vicinity of the rear panel 16.

Referring now to FIG. 8 for a discussion of the pneumatic and hydraulic systems of the invention, it can be seen that there are four distinct fluid paths defined which are involved in the fluid handling pneumatics and hydraulics of instrument 10. These paths or routings comprise (a) the test vessel fill route; (b) the test vessel drain route; (c) the overflow drain route; and (d) the vacuum system.

Solenoid controlled dispenser 148 controls the "fill" functional event directing diluent from the rinse liquid storage vessel 162 to the test vessel 86;

Solenoid controlled dispenser 150 controls the "drain" event where liquid within the test vessel 86 is drained therefrom and directed to the waste receptacle 164;

Solenoid controlled dispenser 152 controls the "overflow" removal event as will be described later; and Solenoid controlled dispenser 154 controls the generation and distribution of vacuum functioning primarily to direct the sample suspension through the sensing aperture 106 from the cuvette 86 to the vessel 100. The dispenser 154 operates in response to a signal from the control circuit 130 to draw a relatively high vacuum momentarily and only when the WBC counting processing is initiated, as will be explained. The dispenser 154 remains energized during the counting cycle during which time the level of vacuum decreases within predefined limits during the actual counting.

Referring first to the test vessel fill route along which rinse liquid is transferred to and through the dispensing head 68 and nozzle 72 into the test vessel 86 when the lid 26 is horizontally oriented and at selected times during the processing of the sample. The solenoid operated dispenser 148 operates to drive the rinse liquid from reservoir 162 along line 178 via fitting 179 to port 180 of manifold 176. The rinse liquid then passes from port 182 along line 184 past check valve 185 to input port 186 of dispenser 148. The fill fluid circuit continues from dispenser 148 via output port 188 past check valve 190 along line 192 to leg 194 of Y tube 196, and then from leg 198 of Y tube 196 along line 200 to conduit 70 to the dispensing head 68 and dispensing nozzle 72 from whence the rinse liquid is dispensed into the test vessel 86.

The test vessel drain route also involves liquid movement, in this instance, from the chamber 202 (which is communicatively coupled to cuvette 86, either directly as an integral part thereof or through a conduit [not shown]), along line 204 past fitting 206 and intercepting check valve 208 to input port 210 of test vessel drain dispenser 150. The output of dispenser 150 is directed from port 212 past check valve 214 along line 216 to port 218 of manifold 176 by way of an internal path to port 220 and thence, past fitting 222 along line 224 to the waste reservoir 164.

A line 226 leads from fitting 84 coupled to overflow well 78 past check valve 230 to input port 232 of overflow drain dispenser 152. Line 234 is coupled to leg 236 of Y tube 196 and leads past choke 238 and check valve 240 to port 242 of overflow drain dispenser 152. Line 244 is coupled between port 246 of overflow drain dispenser 152 and port 248 of manifold 176, passing check valve 247 and thence to the waste reservoir 164.

Line 250 leads from the fitting 252 of vessel 100 to the port 254 of solenoid operated vacuum dispenser 154. Line 256 leads from the port 258 of dispenser 154 to port 260 of the adjustable volume vacuum chamber 114 while line 262 leads from the port 264 of dispenser 154 past check valve 266 to port 268 of the manifold 176. The manifold 142 is coupled to the adjustable volume vacuum chamber 144 by line 269 leading from port 270 to port 272 by way of valve 274 and choke 276 monitored by switch 160 which monitors the level of rinse liquid in reservoir 162. As mentioned earlier, switch 160 is mounted on manifold 142 and in the line running from port 272 to port 280 leading by line 278 to level sensor tube 282. When the dispenser 254 is released, the rinse fluid level is checked by the back pressure generated as a result, which appears at port 260 of chamber 144 via line 256 and is transmitted via port 270 and line 269 through check valve 274 and choke 276 to port 272. The resulting back pressure pulse is applied to the switch 160 and is directed via port 280, line 278, and fitting 281 to emerge from level sensor tube 282.

If the rinse liquid level is below a preset level, back pressure will be absent, therefore, insufficient to maintain the normal closed condition of said switch 160 under the effect of the previously mentioned back pressure pulse originating from dispenser 154. If the switch 160 is not closed by the effect of the aforementioned pressure pulse, the alarm representing the low "diluent" warning will be activated to flash the word "diluent" at the front panel 14 and to cause the alarm device 452 to sound in an interrupted pattern.

Line 284 couples port 286 of the manifold 142 to port 288 of the adjustable volume vacuum chamber 144 while line 290 is connected between port 292 of the manifold 142 and vacuum release solenoid valve 294 by way of choke 298 to a vent 296 to atmosphere. Valve 294 is coupled to filter 299 to prevent entry of dust, etc., into the system during venting.

Provision is made for a direct injection of rinse liquid controlled by solenoid valve 300 coupled by line 302 past check valve 301 to port 304 of the hydraulic manifold 176 and by line 306 to fitting 308 of the vessel 100. This enables sweeping of any residual matter, including bubbles, etc., from the downstream or "waste" side of aperture 106, and helps to bleed the high initially generated vacuum toward the proper operating limits.

In U.S. Pat. No. 3,927,317 there was described circuitry which permits a voltage representing light transmittance of externally supplied blank solution to be electronically stored for a period of time during which a calibration control solution and then a sequence of samples are applied to the photometer for first calibration thereof and then measurement of the sample, both in a rundown mode.

The hemoglobin computing circuitry here provided involves electronic storing first of a voltage value representing a calibration solution having a known HGB value rather than that representing blank during calibration, and as well, a separate calibration operating mode to which reference can be made apart from the testing operation per se.

Figure 6:
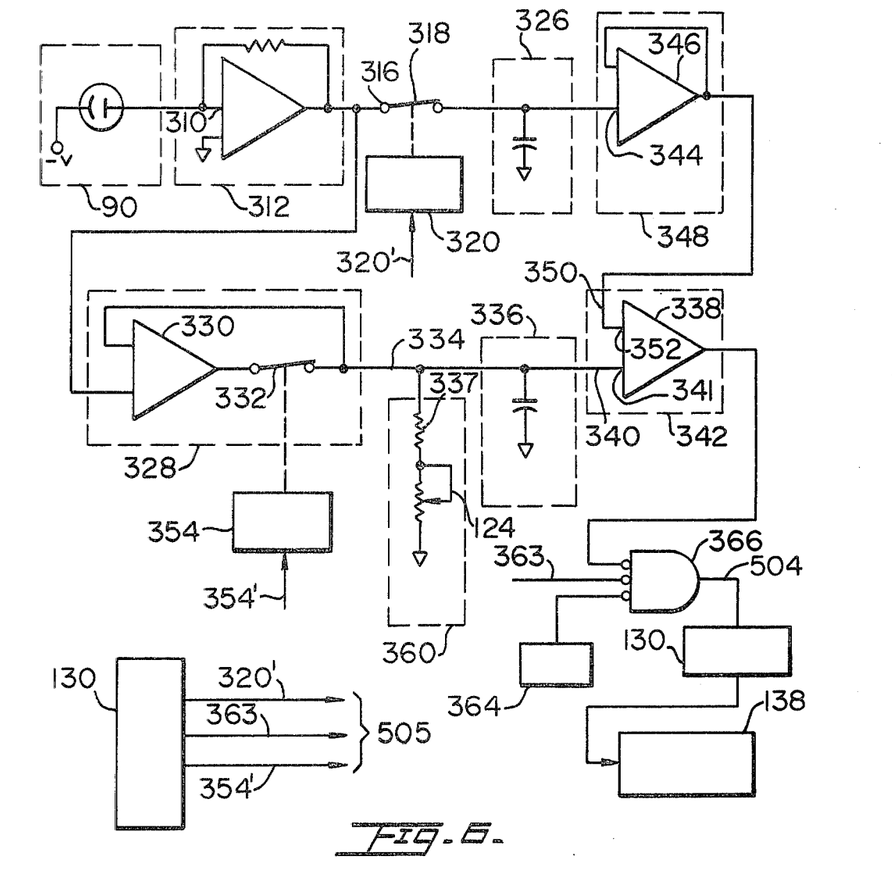
FIG. 6 is a schematic representation of the hemoglobin determining circuitry.

Referring now to FIG. 6, the block diagram is illustrative of the hemoglobin computing circuitry 134 for instrument 10. An output in the form of a current is generated by the photodetector 90, and is proportional to the transmission of a beam 98 of light from the light source 96 passing through liquid media within the test vessel 86. The current is directed to the input 310 of the current to voltage converter 312 where it is converted to a d.c. voltage proportional to light transmittance of said media. The thus converted voltage is directed to the input 316 of first switch 318. Switch 318 is controlled by control circuit 320 and is normally closed for the first half cycle of operation. When switch 318 is closed, the voltage from the converter 312 is placed on the sample storage capacitor 326.

Switch 318 can be closed and opened at any convenient time. The switch 318 is opened just prior to operating test vessel drain dispenser 150. With switch 318 open, the first obtained voltage remains stored in the capacitor 326. The storage capacitor 326 is buffered with a high impedance voltage follower 348.

The dispenser 150 is operated to drain test vessel 86. Dispenser 148 is enabled to fill the drained test vessel 86 with rinse liquid. Dispenser 152 is energized to remove any rinse liquid which may have overflowed into well 76. This process is repeated so that the test vessel is filled twice with rinse liquid and drained once.

The transmittance of the beam 98 now is represented by another d.c. voltage appearing at input 316, directed to switch 318 which is open. Hence, the voltage is directed to voltage follower 328. Voltage follower 328 includes amplifier 330, the output of which is directed to second switch 332 which is within the feedback loop of the voltage follower 328. When switch 332 is closed, the circuit operates as a voltage follower. The output follows the input. Accordingly, with switch 332 closed, the output of amplifier 330 is directed via line 334 to reference storage capacitor 336. The capacitor 336 charges to a voltage value representing the second obtained voltage level which will be higher than or at least equal to the voltage level stored on capacitor 326. At the same time, the voltage from the capacitor 336 is directed to the input 340 of comparator 338 of comparator circuit 342. The voltage on capacitor 326 is directed by input 344 to amplifier 346 of a voltage follower circuit 348. The output of amplifier 346 is directed by line 350 to input 352 of comparator 338 of comparator circuit 342. The opening and closing of switch 332 is controlled by control circuit 354. Both control circuits 320 and 354 can be operated by outputs from the control or programming circuit 130 via lines 320' and 354' respectively, or the switches 318 and/or 332 could be controlled manually.

Switch 332 normally is closed until just before the end of the cycle of operation at which time the desired readout is obtained. When switch 332 is opened, the voltage stored in capacitor 336 "runs down" through resistor 337 and potentiometer 124 (together forming rundown circuit 360). The capacitor 336 discharges to a voltage where the voltage from the voltage follower 348 is the same as that delivered to input 341 of comparator 338. At the time switch 332 is opened, a control signal is directed to gate 366 via line 363 to enable gate 366 so that pulses from a continuously operable oscillator 364 are permitted to pass the gate 366 and to accumulate in readout 138. When voltages are equal at inputs 352 and 341, the output of comparator 338 is directed to the gate 366 to close same, discontinuing the accumulation of the oscillator pulses on readout 138. The number of pulses accumulated in the readout 138 during the time it takes the second obtained voltage on capacitor 336 to discharge to the level of the first obtained voltage on capacitor 326 is directly proportional to the logarithmic ratio of the two voltages and is a measure of the hemoglobin concentration in grams per decaliter.

The invention herein provides a calibration mode of operation separate from the normal or sample testing mode of operation used to perform determinations of WBC and HGB upon unknown samples. The instrument 10 is placed in the calibration mode by manipulation of the three position switch 40. When the lid 26 is raised, the "sample" solution first poured into the test vessel 86 comprises an assayed calibration solution having a known HGB. As described above, a voltage representing the value of the transmittance of light through the test vessel 86 containing the assayed solution is applied to the capacitor 326. The switch 318 is opened, isolating and preserving that voltage on said capacitor 326. The test vessel 86 is drained of said assayed solution and refilled with rinse liquid. The said test vessel again is drained and refilled with the rinse liquid to reduce carryover.

The voltage representing the light transmittance through the rinse liquid is applied by way of follower circuit 328 and closed switch 332 to the capacitor 336, switch 318 being maintained in open condition, preserving the first obtained voltage thereupon. Switch 332 is opened and simultaneously the gate 366 is opened. The voltage upon capacitor 336 then discharges. When the discharging voltage equals the voltage preserved on the capacitor 326, the gate 366 closes. The number of pulses from oscillator 364 which have accumulated on the readout 138 while gate 366 was open should be equivalent to a representative measure of the hemoglobin content of the assayed sample. If not, the variable potentiometer 124 is adjusted to vary the discharge time so that duration of discharge until the voltages on capacitors 326 and 336 are equal is such as to enable the proper accumulation of oscillator pulses on the readout to register the correct readout.

While the instrument 10 is in the calibration mode, the switch 322 is caused to open and to close every other second after the end of the cycle when the readout is obtained. Since the voltage on capacitor 326 is preserved until calibration is completed, successive readouts are displayed every other second. The succession of readouts displayed enables the potentiometer 124 to be adjusted by manipulating shaft 124' thereof from the front of instrument 10 until the correct readout is obtained. Once properly adjusted, the potentiometer 124 no longer is manipulated and the instrument 10 is calibrated as to hemoglobin content measurement.

Figures 6, 6A:
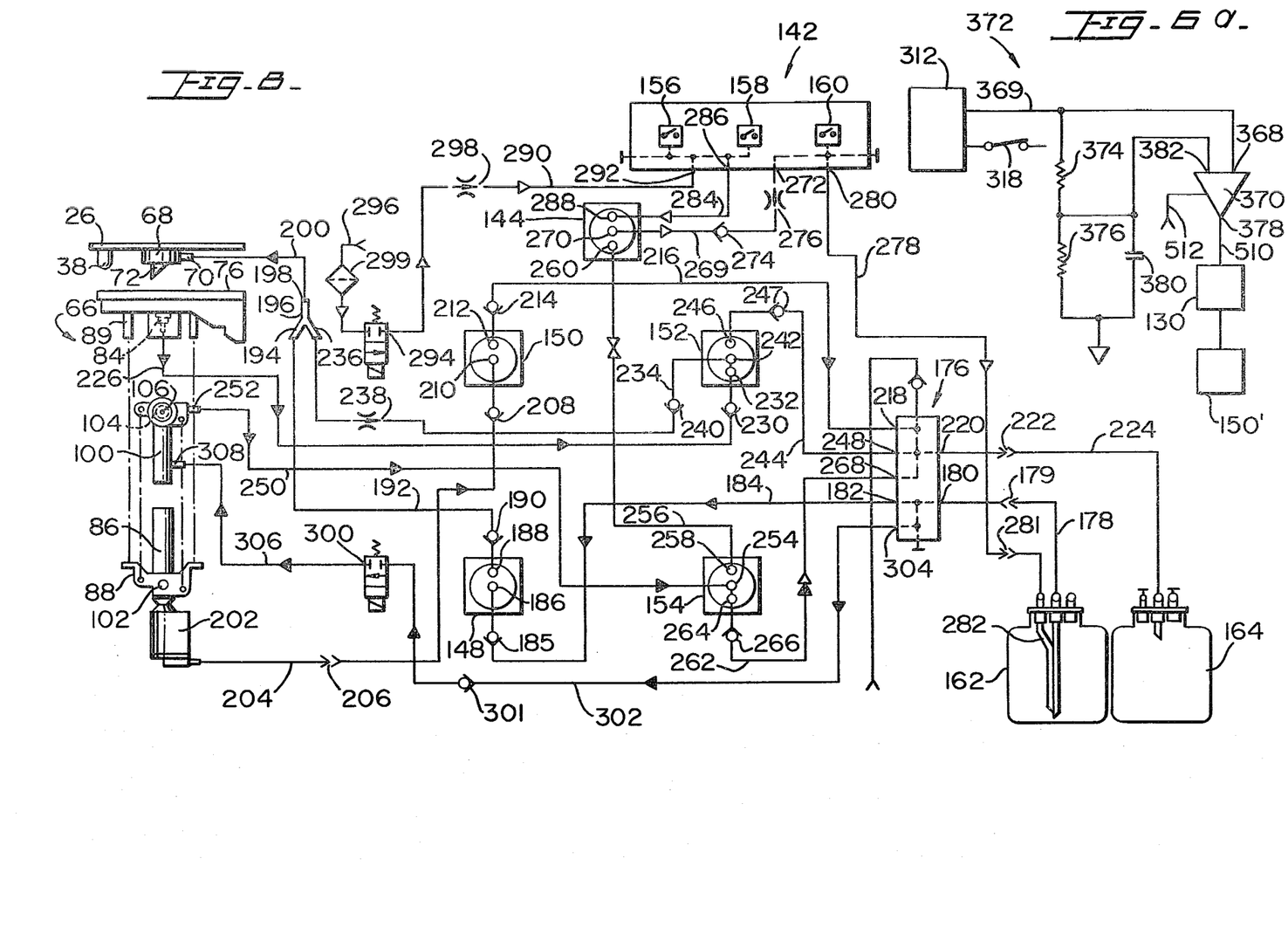
FIG. 6a is a schematic representation of the sample entry detecting circuitry.

Referring to FIG. 6a, a circuit 372 is provided to detect the entry of sample into the test vessel 86. This circuit shall be referred to as the sample entry detector circuit 372. When the lid 26 is raised, the detector circuit 372 is enabled ready to operate by a signal from output 512 of control circuit 130 and the test vessel 86 also is drained. The beam 98 now passes through a different medium, air. The voltage now emanating from the converter 312 is a value less than the voltage resulting when the beam 98 passes through the rinse liquid, the material previously in the test vessel 86. Line 369 directs voltage from the converter 312 to the sample entry detector circuit 372. The voltage is divided between the inputs 368 and 382 of comparator 370 by resistors 374 and 376, with the greater value directed to input 368. The difference between such input values places the comparator output 378 in one state.

When the sample is poured into the test vessel 86, the beam 98 is interrupted by the sample and the voltage from the converter 312 changes in value rapidly. Thus the voltage applied to input 368 of comparator 370 moves below the voltage applied to the input 382 because the voltage on the capacitor 380 cannot change as rapidly. Hence, the comparator 370 changes state with the output 378 therefrom directed to the control circuitry 130 to result normally in momentary energization of drain dispenser 150 to cause a small portion of the sample to be drained from the test vessel 86 while it is being poured. The timing of the operation of the drain dispenser 150 can be controlled so that the amount of said portion drained can be varied. A full drain can be effected if desired. The key advantage hereto is that the sample itself is being used as the wash per se, flushing the test vessel 86 of possible residual liquid, etc., reducing carryover and thus increasing the precision capable of being realized by the instrument 10.

It should be understood that the detection effected by circuit 372 need not be limited to detection upon pouring of the sample into the test vessel but can be utilized to detect any entry of sample to the test vessel by any other means and effect washing with the sample.

Switch 40 now can be changed over to the normal or "run" mode. The instrument 10 now is ready for repeated determinations for unknowns without requiring repeated calibration for a considerable additional number of further unknowns. If it is desired to check on the calibration, all that is necessary is to make a run through with the assayed solution.

When either sample or rinse liquid is introduced to the test vessel 86, a portion may overflow into the well 78. Operation of overflow dispenser 152 directs such overflow to the waste reservoir 164.

Figure 5B:
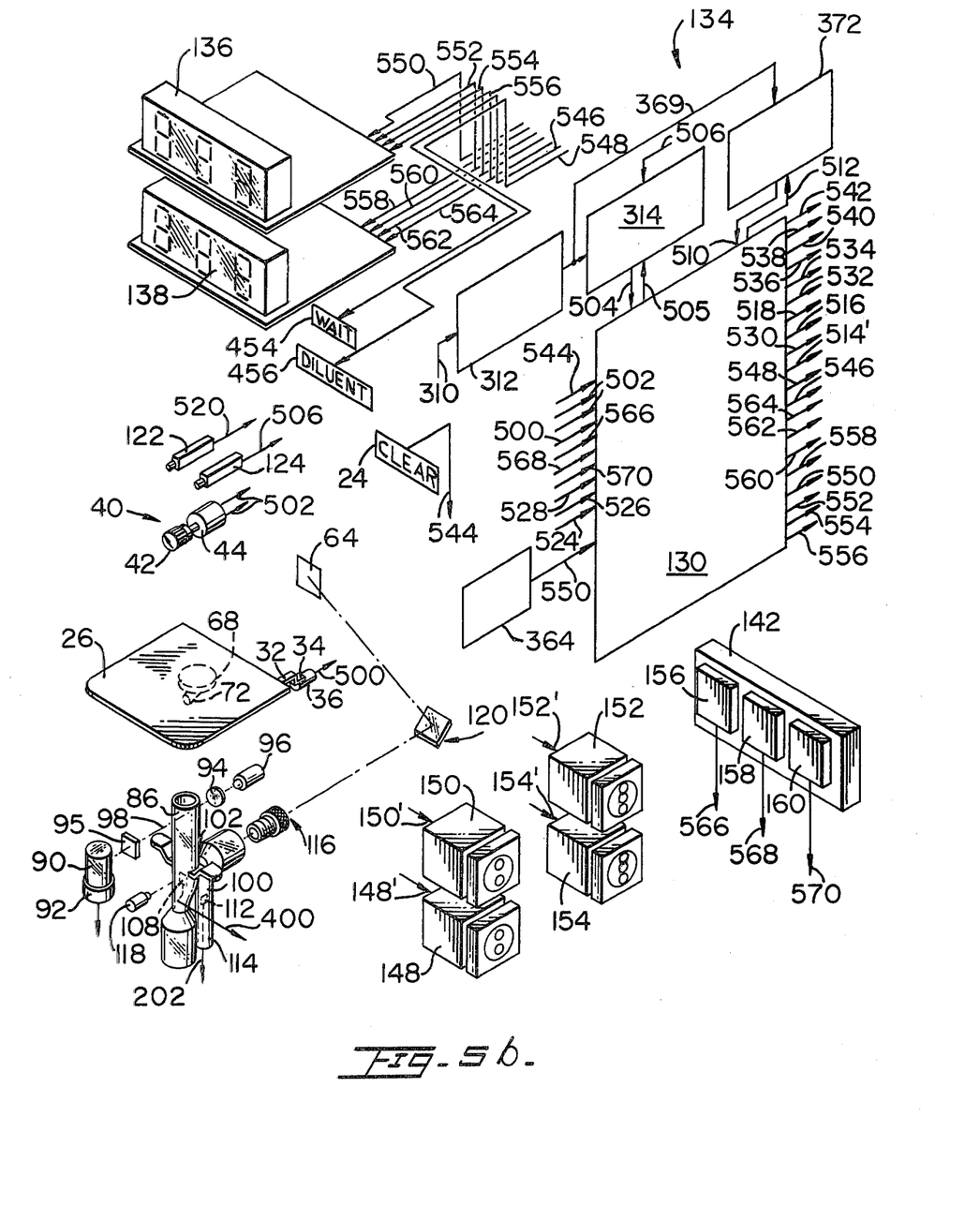
FIG. 5b is a block diagram illustrating the remaining portion of the operational system of the instrument embodying the invention.
Figure 7:
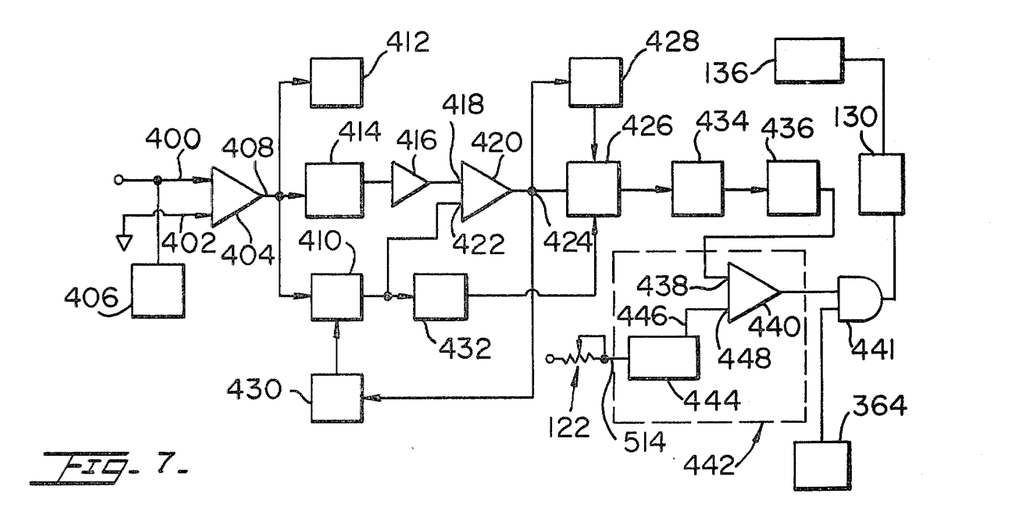
FIG. 7 is a block diagram illustrating the WBC processor circuitry of the instrument embodying the invention.

Attention now is directed to FIGS. 5a, 5b and 7 wherein the WBC processing circuitry and the accompanying vessel and electrode system are diagrammatically set forth, same operating on the Coulter principle. According to said established principle, a suspension of particles (i.e. here white blood cells which remain after a blood sample has been diluted with a conductive diluent and lysed with a lysing agent to break down and red cell walls and release the hemoglobin content thereof) is caused to flow through the scanning aperture 106 from test vessel 86 to vessel 100. At the same time, an electric current is caused to flow through the scanning aperture 106 from electrode 108 to electrode 112. Each time a particle passes through the aperture 106, it causes a change in the impedance of the effective volume of suspension contained within the aperture. Such change produces a signal whose amplitude is proportional to the volume of the particle and whose duration is equal to the time during which the particle traverses the aperture 106. Such signals are electronically counted for producing a "WBC" (White Blood Cell Count).

As referenced above, the WBC processor circuitry 132 substantially is similar to the WBC processor circuitry disclosed in U.S. Pat. No. 3,733,548.

Referring to FIG. 7, the signal from the aperture 106 is received by input terminals 400 and 402 of amplifier 404, the current being supplied by aperture current supply 406. The output 408 of amplifier 404 is directed to the half-height detector 410 and to blockage detector 412, as well as to the delay circuit 414. The output of the delay circuit 414 is directed to compensation amplifier 416 and thence to terminal 418 of comparator 420. The output of the half-height detector 410 is directed to the other terminal 422 of comparator 420. The output of the comparator 420 appears at junction 424 and is directed to the editor circuit 426, to the long pulse inhibitor 428 and back to the trailing edge detector 430.

The long pulse inhibitor circuit 428 monitors and eliminates pulses of too long duration which would not represent passage of a particle through the aperture.

The output of the half-height detector 410 also is directed by way of plural threshold detectors 432 to the editor circuit 426. The half-height detector 410 is equivalent to the pulse stretcher and attenuator of FIG. 3 of U.S. Pat. No. 3,733,548.

The output of the editor 426 is directed to the integrator 434, and through coincidence correction circuit 436 to one terminal 438 of comparator 440 of the analog to digital converter 442. The converter 442 includes a ramp generator 444, the output 446 of which is connected to the other terminal 448 of said comparator 440.

The output of the comparator 440 provides a pulse, the width of which will allow a number of pulses from oscillator 364 to pass through a gate 441 to readout 136, the number of which is representative of the number of particles that have passed through aperture 106.

An alarm circuit 450 (FIG. 5a) operates an alarm device 452 to issue different audible indications of certain functional conditions which should be called to the attention of the operator of instrument 10. One of such conditions involves monitoring the cadence of the count to provide indication of a condition where the count is not truly indicative of the actual particles passing through the aperture 106, such as when debris blocks or partially blocks the aperture. The count accumulates at a fairly steady rate; deviation from such rate can be heard from the audible device 452. The audible device 452 is heard as a series of "pops", each occurring after a specific number of counts have been recorded. One example offers a "pop" at each one-thousand counts.

A particular advantage of the vacuum system employed herein is that vacuum is drawn during each cycle only when vacuum is required to draw suspension through the aperture for particle counting. Provision of such system eliminates the necessity of using a continuously operating vacuum pump and the auxiliary hardware needed therefor.

Figure 4:
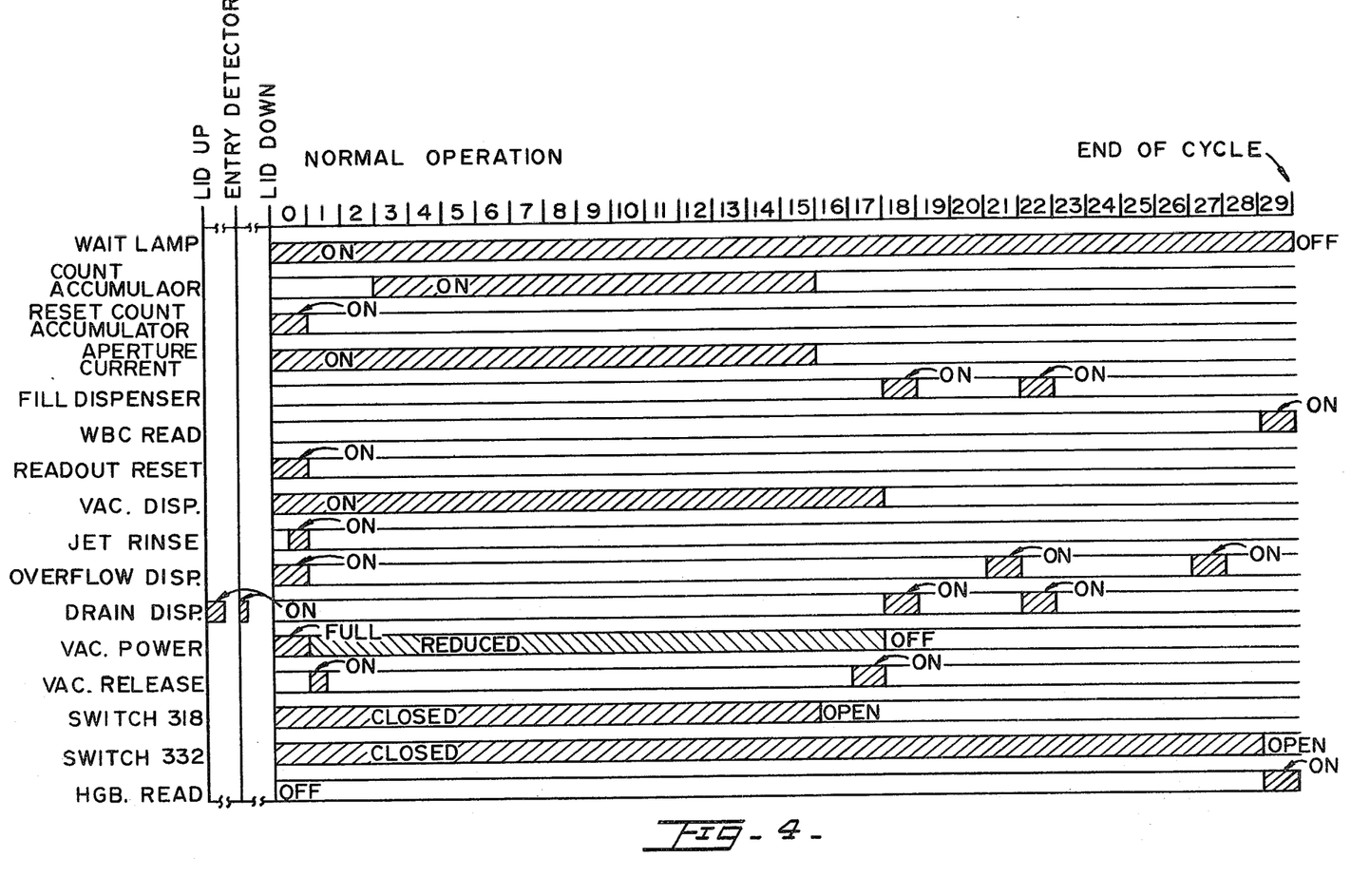
FIG. 4 is a timing chart illustrating the sequence of events during the operation of the instrument embodying the invention.

It shall be helpful to review the operation of instrument 10 by reference also to the timing chart of FIG. 4.

The operation is initiated by lifting the lid 26 which energizes the drain dispenser 150, drawing the rinse liquid which had remained in the test vessel 86 after the previous determination into the chamber of said dispenser 150. One second later, the dispenser 150 is de-energized to direct the liquid from its chamber to the waste receptacle 164. The unknown sample is poured into the test vessel 86. The photometric monitoring apparatus, i.e., photodetector 92, etc., senses the interruption of beam 98 and activates the sample entry detecting circuitry 372. The dispenser 150 is energized again for approximately 140 milliseconds to cause approximately the first cubic centimeter of sample to be drained from the test vessel 86 as it is being poured. The dispenser 150 is actuated again by the normal control circuit 130 for two one-second intervals later in the cycle so as to drain the test vessel 86 of sample and of the first rinse, when the occasion therefor arises during said cycle.

The pouring of the sample into the test vessel 86 may result in some overflow, the overflow liquid entering well 78. When the lid 26 is lowered, the dispenser 152 is operated to draw the overflow from the well 78 entering the chamber of dispenser 152. One second later, the dispenser 152 is released, discharging the liquid from its chamber to the waste receptacle 164. Dispenser 152 is actuated again for two one-second intervals also later in the operating cycle to remove the overflow which occurs during the rinsing of the test vessel 86.

As noted in the normal operational chart of FIG. 4, the vacuum is generated and used only when required to draw sample through the scanning aperture 106 for WBC determination. The vacuum source used is solenoid actuated vacuum dispenser 154 which is energized when the lid 26 is lowered after the sample has been poured into the test vessel 86. The vacuum dispenser 154 operates to draw a vacuum higher than required for normal operation. One-half second later, the jet-rinse solenoid valve 300 operates to direct rinse liquid from vessel 162 to the scanning aperture 106 clearing the same of any debris or bubbles, also reducing the level of vacuum slightly toward the normal range.

After one-half second, the jet-rinse solenoid valve 300 is de-energized, and simultaneously, the vacuum release valve 294 is energized, venting the vacuum system to atmosphere momentarily. This causes the vacuum level in the vacuum system to deplete toward 6.75 inches of mercury, the upper level which is desired to be used to move particles through the scanning aperture 106 during the counting of the particles in determining WBC. Now, when the desired upper limit or vacuum level is reached, the switch 158 operates to de-energize the vacuum release valve 294, halting the depletion of the vacuum in the system, except for the depletion caused by the passage of the sample through the scanning aperture 106.

By nature of the electrical solenoid used with dispenser 154, full power thereto is required during initial energizing of the solenoid. Hence, after energization of said solenoid, the power thereto is reduced.

The vacuum capable of being generated by the vacuum dispenser 154 is dependent upon the atmospheric pressure. An adjustable volume chamber 144 is interposed in the system and is used to compensate for differences in atmospheric pressure at the location of use of the instrument 10 by changing its interior volume accordingly. Both the test switches 158 (the upper limit switch) and 156 (the lower limit switch) are checked for proper function during each cycle of operation by verifying that they change from open to closed condition as the vacuum dispenser 154 is energized. If the vacuum release solenoid valve 294 is still energized when the counting begins, three seconds after the lid 26 has been lowered, and if the vacuum in the system has failed to reach the desired upper level, whether due to the malfunction of said vacuum release solenoid valve 294 or misadjustment of the adjustable vacuum chamber 144, the audible device 452 is sounded by alarm circuit 450.

Counting begins three seconds after lid 26 is lowered and continues for thirteen seconds during which time the flow of sample through the scanning aperture 106 causes the vacuum level to deplete gradually. Should the vacuum level deplete below 5.5 inches Hg. during the counting period, the limit switch 156 will open, sounding the audible device 452. If the lid 26 is raised and lowered without addition of sample, air will enter the aperture 106, which will deplete the vacuum prematurely and activate the circuit 450 and sound the alarm device 452. This is the same alarm device 452 which was discussed earlier as operating to monitor the count cadence.

At the end of the count cycle, the vacuum release solenoid 294 again is energized to vent the system to near atmospheric pressure. One second later, both the dispenser 154 and the vacuum release solenoid 294 are released causing a pressure pulse which dispels the liquid which has accumulated in its chamber through valve 266 and manifold port 268 to the waste receptacle. The momentary pressure pulse also puts a back pressure on the aperture 106 to help to clear same of any debris which may be present and also helps to keep the aperture 106 clear.

Manual clearing of the aperture 106 of debris, bubbles, etc., is accomplished by actuating the push button switch 24 which causes the vacuum dispenser 154 and the vacuum release solenoid valve 294 to be actuated and released simultaneously, thereby to cause the aforementioned pressure pulse to be generated.

During the measuring cycle, and in fact, 18 seconds after the lid 26 is lowered, the fill dispenser 148 is energized, causing rinse liquid to be drawn from reservoir 162 into its chamber. Simultaneously, the drain dispenser 150 is energized to drain the test vessel 86 of sample by way of chamber 202. One second later, both dispensers 148 and 150 are released. The rinse liquid in the chamber of dispenser 148 is directed to the nozzle 72 and introduced into the test vessel 86. The old sample is discharged into the waste receptacle 164. Three seconds later, the rinse and drain cycle is repeated to assure complete rinse of the test vessel 86, leaving a second volume of rinse liquid within said test vessel 86. The drop of liquid which may be left on the tip of the nozzle 72 is removed by connecting choke 238 and check valve 240 in series to the overflow dispenser 152 and to the delivery line for rinse liquid at the Y-fitting 198. The small amount of rinse liquid thus is retracted from the tip of nozzle 72 so that it does not dilute the sample by falling from the tip of nozzle 72 into vessel 86.

The control circuitry 130 comprises logic circuitry which receives input pulse signals at preselected intervals evidencing performance of a function or a series of functions; and, either upon the receipt of a particular input signal or in line with a preselected timed program, issues output signals to the various functional elements of the apparatus.

The control circuitry 130 is illustrated in block form in FIG. 5b with the inputs and outputs represented in flow form. The raising and lowering of the lid 26 operates switch 36 which feeds to input 500 of the control circuit 130.

As mentioned earlier, the three-position switch 40 is operated to place the instrument in one of the operational modes: the normal or "sample run" mode, the calibration operational mode, or the prime operational mode. When the instrument first is used, say after inactivity, switch 40 is operated by manipulation of knob 42 to place the instrument in the prime mode, directing a signal to the control circuit 130 via lines 502. In this mode, the fill dispenser driver 148' is energized to enable dispenser 148 to fill all elements of the hydraulic system with rinse liquid from reservoir 162. Plural fill and drain cycles automatically are performed all with the lid 26 in horizontal orientation. The switch 40 next is placed in the calibrate mode and the known or calibration solution is poured into test vessel 86. Converter 312 operates to feed both the HGB computing circuit 314 and, via line 369, the sample entry detector circuit 372. Inputs from control circuit 130 to the HGB computing circuit 314 are represented by line 505 and outputs from circuit 314 to control circuit 130 are represented by line 504. The HGB calibration potentiometer 124 provides an input 506 to the HGB circuit 314.

The sample entry detector 372 signal is fed to input 510 of the control circuit 130 and receives an output 512 from the control circuit 130.

There are illustrated four outputs (550, 552, 554, 556) from the control circuitry 130 to the WBC readout 136 and four outputs (558, 560, 562, 564) from the control circuitry to the HGB readout 138.

There are four outputs from the control circuit 130 to the WBC processor; one, 530 is directed to the aperture current supply 406 causing the current flow across the aperture. An output signal along line 514 is directed to ramp generator 444; an output signal along line 516 is directed to one input or terminal of the integrator 434; output 518 leads to the other input terminal of the integrator 434; line 520 connects the WBC potentiometer to the input of ramp generator 444; line 522 connects the WBC comparator 440 output to the input 524 of control circuit 130. The output of the editor 426 is directed to input 526 of control 130.

The blockage detector 412 is connected to input 528 of the control circuit 130 and output 518 from the control circuit 130 is linked both to the blockage detector 412 and to one terminal of the integrator 434 for resetting each.

Output 532 from control circuit 130 is connected to the driver 150' for the center drain dispenser 150.

Output 534 from control circuit 130 is connected to the input of the power reducer 151 which in turn is connected to the driver 154' of vacuum dispenser 154.

Output 536 from control circuit 130 is connected directly to the input of the driver 154'.

Output 538 from the control circuit 130 is connected to driver 148' for the fill dispenser 148 and output 540 is connected from the control circuit 130 to the driver 152' for overflow dispenser 152.

Output 542 is connected to the alarm circuit 450 which operates audible alarm device 452 when energized. Clear button 24 has an input 544 to the control circuit 130.

Outputs 546 and 548 are coupled from the control circuit 130 to the lamps representing the wait signal monitor 454 and low rinse liquid monitor 456. Control inputs 566, 568, and 570 respectively lead from switches 156, 158, and 160.

The oscillator and frequency divider circuitry 364 is coupled to input 550 of control circuit 130.

When lid 26 is lowered, all digits are set to zero and remain at zero until readings are taken at the end of the cycle. The readout circuitry is constructed so that when lid 26 is raised, the readouts 136 and 138 all read a full segmented digit, i.e., 8, so that the operator may visually ascertain if all the segments of each digit are operable. This assures against incorrect readings due to illuminated segment portion failure.

If larger than normal particles such as large bubbles or debris pass through aperture 106, the blockage detector 412 may be energized to cause the readouts to flash repeatedly so that the operator is alerted that a blockage may have occurred which would cause the readout value to be erroneous. The operator then has a choice of accepting the result or re-running the particular sample. The flashing readout may be cleared by activation of clear button 24. Also, the readout 136 has an upper limit of $50 \times 10^3$ counts per $mm^3$ and the readout 138 has an upper limit of 50 grams per decaliter HGB. If such limits are exceeded, the affected readout will display a warning such as an alphanumeric representation to alert the operator, for example, "FF.F".

The instrument herein described is capabel of minor modification and variation in construction without departing from the spirit and scope of the invention as defined in the appended claims.

What we claim is:

1. In an electronic particle analysis apparatus wherein there is provided a hydraulic and pneumatic system for moving fluids by hydraulic means and by pneumatic means from selected locations to predetermined destinations in accordance with a selected operating cycle and wherein a vacuum level is to be established for employment only to perform selected functions during said operational cycle, the improvement comprising vacuum generating means for establishing said vacuum and control means coupled thereto for operating said vacuum generating means to draw vacuum only when vacuum is required to move fluid through scanning aperture means for particle study during said operational cycle.

2. The invention as claimed in claim 1 in which said vacuum generating means comprises a solenoid operated vacuum dispenser.

3. The invention as claimed in claim 1 in combination with first and second vessels, said first vessel having a particle suspension therein, scanning aperture means defining the sole communication between said first and second vessels, and means coupling said vacuum generating means to said vessels to move liquid therein from said first vessel through said scanning aperture means only during a selected part of said operational cycle, passage of said suspension for a given time period through said scanning aperture means being monitored to provide a count of said particles.

4. The invention as claimed in claims 1, 2 or 3 in which means are provided for controlling the degree of vacuum between selected upper and lower limits suitable for performing said liquid movement.

5. The invention as claimed in claims 1, 2 or 3 in which means are provided for controlling the degree of vacuum between upper and lower limits suitable for performing said liquid movement, said last means comprising selectively operable vent means for reducing the initially generated vacuum level to a defined limit.

6. The invention as claimed in claim 5 in which there is provided means for sensing the defined vacuum level limits and alarm means operated by said sensing means for indicating when the vacuum level is outside said limits.

7. The invention as claimed in claims 1, 2 or 3 in which an adjustable volume vacuum chamber is coupled within said pneumatic system to said vacuum generating means, and means for changing the volume of said vacuum chamber dependent upon the atmospheric pressure at site of use whereby to render the limits independent of changes in ambient atmospheric pressure at different sites of use.

8. The invention as claimed in claim 3 wherein said hydraulic means of the hydraulic and pneumatic system includes plural and solenoid controlled, hydraulically operated dispensers each coupled with a source of liquid, a coupling at said first vessel and a destination to perform a specific functional operation during the operational cycle including, respectively, rinsing of said first vessel with rinse liquid from a source thereof, draining said first vessel of liquid therein, and removing liquid which may have overflowed at the vicinity of said first vessel, and control means adapted to operate said respective dispensers at preselected intervals during the operational cycle.

9. The invention as claimed in claim 3 and means operable to drive liquid from said second vessel to said first vessel through said scanning aperture means at a selected time during said operational cycle for clearing said scanning aperture means.

10. The invention as claimed in claim 3 and first and second valve means coupled in said pneumatic means, said first valve means operable to introduce liquid to said pneumatic means and to said second vessel to direct said liquid toward said scanning aperture means and simultaneously to serve to reduce the generated vacuum level to the upper operational vacuum level limit and said second valve means operable to vent said pneumatic means to atmosphere at a selected time during said operational cycle.

11. The invention as claimed in claim 3 and means coupled to said first vessel for draining at least a portion of its contents therefrom and directing said drained portion to a waste receiver at a selected time during said operational cycle.

12. The invention as claimed in claim 11 in which said drained portion comprises the entire content of said vessel at the time of drain, and means to drain at least a portion of a second liquid commencing as the second liquid is introduced into said test vessel.

13. The invention as claimed in claim 12 in which said last mentioned portion is drained while the second liquid is being introduced into said test vessel.

14. The invention as claimed in claim 3 and in combination therewith, optical hemoglobinometer means for determining the hemoglobin content of a liquid sample suspension introduced into the said first vessel.

15. The invention as claimed in claims 3 or 14 and means for reducing carryover of a prior liquid to the next successively introduced liquid in said first vessel by draining at least a portion of last mentioned liquid from said test vessel.

16. The invention as claimed in claims 3 or 14 and means for reducing carryover of a prior liquid to the next successively introduced liquid in said first vessel by draining at least a portion of said last mentioned liquid from said test vessel immediately subsequent to its introduction to said test vessel.

17. The invention as claimed in claims 3 or 14 and means for reducing carryover of a prior liquid to the next successively introduced liquid in said first vessel by draining at least a portion of said last mentioned liquid from said test vessel simultaneously with its introduction.

18. The invention as claimed in claims 3 or 14 and means for reducing carryover of a prior liquid to the next successively introduced liquid in said first vessel by draining at least a portion of said last mentioned liquid from said test vessel, said portion comprising the full amount of second liquid introduced, the second liquid being re-introduced subsequent to said drain.

19. The invention as claimed in claims 3 or 14 and means for reducing carryover of a prior liquid to the next successively introduced liquid in said first vessel by draining at least a portion of said last mentioned liquid from said test vessel simultaneously with its introduction and electrical circuit means for detecting entry of said second liquid into said test vessel and causing said drain when such entry is detected.

20. The invention as claimed in claim 3 and an optical hemoglobinometer for determining hemoglobin content of a liquid introduced to said first vessel, said hemoglobinometer including means for monitoring transmittance of a beam of light through said first vessel and generating an electrical signal representative of the transmittance of at least a pair of liquids successively introduced into said first vessel, means for converting the signals representing each of said pair of liquids into respective pairs of d.c. voltages, one of said voltages having a lower voltage than the other of said pair and being applied to a first storing means, the second and higher of said voltages being applied to a second storing means, means for preserving the first voltage on said first storing means, means for comparing the first and second voltages, means for discharging said second voltage until a balance of said first and second voltages occurs, means for displaying the duration of said discharge, means to adjust the duration of said discharge on the second storing means for calibration of said device, and means to provide repetitive readout displays for reference thereto during the adjustment of the duration of said discharge.

21. The invention as claimed in claim 20 and oscillator means generating a continuous series of pulses, accumulating readout means to receive and visually display the accumulated number of said pulses, gate means interposed between said oscillator means and said accumulating readout means and operable upon initiation of said discharge to pass pulses to said readout means, said second voltage being discharged to a value equal to the first voltage and said gate means being blocked upon reaching of said last value.

22. In the combination of an electronic particle counting apparatus and an optical hemoglobinometer for providing respectively white blood cell count and hemoglobin content of a sample suspension as readable displays, the counting apparatus being of the type wherein particles of the sample suspension are caused to move through a scanning aperture whose effective impedance is changed with the passage of each particle therethrough, the change of impedance generating an electrical signal which can be counted, the improvement comprising said apparatus including a test vessel for receiving said sample suspension, a second vessel adjacent said test vessel, photometric means for monitoring said suspension when same is within said test vessel, scanning aperture means carried by at least one of said vessels and defining the sole communication therebetween, means, including electrode means, for establishing a current path within said scanning aperture means and between said vessels, means for monitoring and recording passage of particles through said scanning aperture means and circuit means coupled to readout means for receiving, accumulating and converting signals representing passage of said particles into a readable display, a pneumatic system operable to move sample suspension from said test vessel to said second vessel and a hydraulic system operable to move liquids from a source to and from said test vessel, said pneumatic system including a solenoid operated vacuum generating means coupled to said vessels and means to operate said vacuum generating means to generate a vacuum in accordance with a predetermined operating cycle only when vacuum is required to move the sample suspension through the scanning aperture.

23. The combination as claimed in claim 22 and said optical hemoglobinometer includes means for generating an electrical signal representative of the transmittance of said sample suspension in said vessel and that of a second liquid introduced successively therein, means for converting the signals representing each of said transmittances into respective pairs of d.c. voltages, the first one of said voltages having a lower voltage than the second and being applied to first storing means, the second of said two voltages having a higher value than the first and the higher of said voltage values being applied to a second storing means, means for comparing the first and second voltages, means for discharging the second voltage until the first and second voltages are equal and balance on said comparing means is reached, and readout means to display the duration of said discharge.

24. The combination as claimed in claim 23 and oscillator means generating a continuous series of pulses, gate means interposed between said oscillator means and said readout means and operable upon initiation of discharge to pass pulses to said readout means and to block passage of pulses to said readout means when balance is reached.

25. The combination as claimed in claim 23 and means establishing a calibration cycle, said sample suspension comprising a calibration solution having a known hemoglobin content, and means selectively operable during said calibration cycle for preserving the lower of said voltages on said first storing means, means for adjusting the duration of discharge of said second storing means to provide a readout representative of said known hemoglobin content and means for providing repetitive closely spaced readout displays for reference thereto during the adjustment of said last mentioned discharge duration.

26. The combination as claimed in claim 22 or 23 in which said hydraulic system of the hydraulic and pneumatic system includes means for introducing rinse liquid from a source thereof to said test vessel at selected time intervals, means for draining said test vessel also at selected time intervals and said last mentioned means being operable to effect at least a fractional drainage of said test vessel subsequent to the introduction of said liquid therein whereby to reduce carryover between successive introduction.

27. The combination as claimed in claim 22 in which said test vessel is drained, and a second liquid is introduced from a source thereof to said test vessel to replace said drained liquid, means for draining at least a fractional portion of said second introduced liquid from said test vessel upon introduction of said second liquid thereto.

28. The combination as claimed in claim 27 in which said second liquid portion is drained during introduction of said second liquid portion.

29. The combination as claimed in claim 27 in which said second liquid portion is drained immediately subsequent to its introduction.

30. The combination as claimed in claim 22 and valve means for coupling said pneumatic system into said hydraulic system selectively to bleed said pneumatic system to reduce the initially generated vacuum to selected operating vacuum level limits, said valve means operable also to direct the bleed from said pneumatic system to the vicinity of scanning aperture for flushing said vicinity at a selected time during said operational cycle.

31. The combination as claimed in claim 22 in which manually actuatable means are provided for flushing fluid through the scanning aperture means from the second vessel to the first vessel.

32. The combination as claimed in claim 22 or 23 and an adjustable volume vacuum chamber coupled to said vacuum generator.

33. The combination as claimed in claim 22 or 23 and said hydraulic system includes a solenoid controlled dispenser operable at a selected time during the operating cycle to drain overflowed liquids from the vicinity of said test vessel.

34. The combination as claimed in claim 22 or 23 and means to provide an audible periodic indication of the particle count whereby abnormalities therein may be detected.

35. The combination as claimed in claim 22 and electrical circuit means for detecting entry of the sample suspension into the test vessel, means for draining at least a portion of said sample suspension from said test vessel upon detection and prior to moving said sample suspension through the scanning aperture.

36. The combination as claimed in claim 35 which includes means for monitoring the transmittance of a beam of light through said test vessel, and said entry detecting circuit is enabled to cause said draining means to operate when said light beam is interrupted.

37. The combination as claimed in claim 23 and electrical circuit means for detecting entry of the suspension into the test vessel, means for draining at least a portion of said sample supension from said test vessel upon detection and prior to moving said sample suspension through the scanning aperture.

38. The combination as claimed in claim 37 which includes means for monitoring the transmittance of a beam of light through said test vessel, and said entry detecting circuit is enabled to cause said draining means to operate when said light beam is interrupted.

* * * * *